(12) United States Patent
Jensen et al.

(10) Patent No.: US 7,758,529 B2
(45) Date of Patent: Jul. 20, 2010

(54) SYSTEMS AND METHODS FOR IMPROVED OFF-WEIGHTING

(75) Inventors: Jeffrey L. Jensen, Evergreen, CO (US); Brian D. Gillin, Parker, CO (US); John V. Atanasoff, II, Boulder, CO (US); Thomas E. Gage, Boulder, CO (US)

(73) Assignee: Medefficiency, Inc., Wheat Ridge, CO (US)

( * ) Notice: Subject to any disclaimer, the term of this patent is extended or adjusted under 35 U.S.C. 154(b) by 183 days.

(21) Appl. No.: 11/836,673

(22) Filed: Aug. 9, 2007

(65) Prior Publication Data

US 2008/0039758 A1    Feb. 14, 2008

Related U.S. Application Data

(60) Provisional application No. 60/821,940, filed on Aug. 9, 2006.

(51) Int. Cl.
*A61F 5/00* (2006.01)
(52) U.S. Cl. .............................. 602/27; 602/8
(58) Field of Classification Search ............... 602/5, 602/23–28, 60–62, 8, 16; 128/882
See application file for complete search history.

(56) References Cited

U.S. PATENT DOCUMENTS

| | | | |
|---|---|---|---|
| 2,516,872 | A | 8/1950 | Hauser et al. |
| 2,582,242 | A | 1/1952 | Eberl |
| 3,307,537 | A | 3/1967 | Simon et al. |
| 4,628,917 | A | 12/1986 | Campagna, Jr. et al. |
| 4,668,563 | A | 5/1987 | Buese et al. |
| 4,888,225 | A | 12/1989 | Sandvig et al. |
| 5,158,530 | A | 10/1992 | Conklin |
| 5,228,164 | A | 7/1993 | Graf et al. |
| 5,273,802 | A | 12/1993 | Scholz et al. |
| 5,514,080 | A | 5/1996 | Blott et al. |
| 5,637,077 | A | 6/1997 | Parker |
| 5,827,210 | A | 10/1998 | Antar et al. |
| 5,842,475 | A | 12/1998 | Duback et al. |
| 5,957,871 | A | 9/1999 | Darcey |
| 5,980,474 | A | 11/1999 | Darcey |
| 6,022,331 | A | 2/2000 | Darcey |
| 6,159,877 | A | 12/2000 | Scholz et al. |

(Continued)

OTHER PUBLICATIONS

International Search Report for International Application No. PCT/US07/75629, mailed Feb. 22, 2008.

*Primary Examiner*—Michael A. Brown
(74) *Attorney, Agent, or Firm*—Faegre & Benson LLP

(57) ABSTRACT

Embodiments of the present invention include an apparatus for encouraging compliance with a prescribed orthotic treatment, including an orthotic device applied to a limb of a user, a strap coupled to the orthotic device, the strap having two ends and configured to wrap around the orthotic device at an attachment area, where a length along the strap is smaller than a maximum circumference of the limb distal to the attachment area, and a locking mechanism to lock the strap onto itself. Other embodiments of the present invention include a system for off-weighting a user's foot, including a hardenable cast; a rigid outer boot having a footbed, a first side strut with a first strap aperture, a second side strut with a second strap aperture, and a strap extending through the first strap aperture and the second strap aperture and operable to tighten around the hardenable cast.

15 Claims, 12 Drawing Sheets

U.S. PATENT DOCUMENTS

| | | |
|---|---|---|
| 6,228,044 B1 * | 5/2001 | Jensen et al. ............... 602/27 |
| 6,558,339 B1 | 5/2003 | Graham |
| 6,585,671 B2 | 7/2003 | Rhee |
| 6,682,497 B2 | 1/2004 | Jensen et al. |
| 6,716,186 B1 | 4/2004 | Singh et al. |
| 6,942,628 B1 | 9/2005 | Watson |
| 6,945,946 B2 | 9/2005 | Rooney |
| 6,974,431 B2 | 12/2005 | Jensen et al. |
| 2003/0093025 A1 * | 5/2003 | Rhee ............... 602/62 |
| 2004/0210177 A1 | 10/2004 | Grim et al. |
| 2005/0182345 A1 | 8/2005 | Termanini |
| 2005/0240133 A1 * | 10/2005 | Rooney ............... 602/23 |

* cited by examiner

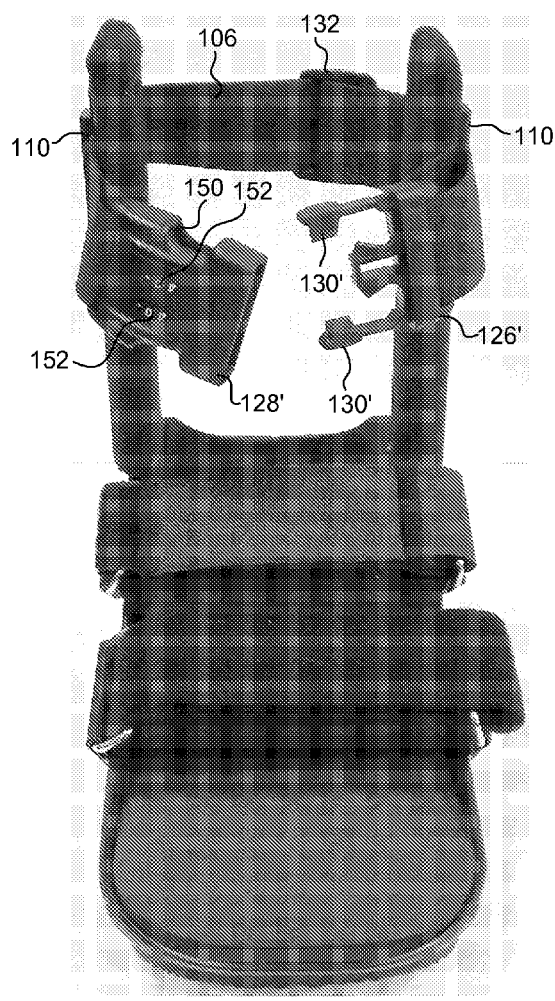 
FIG. 5          FIG. 6

SYSTEMS AND METHODS FOR IMPROVED OFF-WEIGHTING

CROSS-REFERENCE TO RELATED APPLICATIONS

This application claims the benefit of U.S. Provisional Patent Application Ser. No. 60/821,940, filed on Aug. 9, 2006, and entitled, "Total Contact Cast Off-Weighting Systems and Methods," which is herein incorporated by reference in its entirety.

TECHNICAL FIELD

Embodiments of the present invention relate generally to limb off-weighting, and more specifically to systems and methods for treating foot ulcerations with a hard inner cast coupled to a hard outer boot shell.

BACKGROUND

The present invention relates generally to limb off-weighting utilized for the treatment of ulcerations and/or injuries to the plantar area of the foot. The development of effective means for treating foot sores or ulcerations, especially diabetic foot ulcerations, presents a significant medical challenge. Diabetic foot ulcers result in numerous lower extremity amputations per year and account for more hospitalizations than any other single complication of diabetes. A large percentage of diagnosed diabetics suffer from foot ulcerations. In fact, foot ulcers are the leading cause of hospitalization of patients with diabetes and account for a significant percentage of the costs related to diabetic care.

The burdens of such complications can also have a devastating effect on patients and their families. Patients' quality of life can rapidly decline leaving them unable to work, and dependent on family members to spend their time and resources caring for the patient. The problem is compounded by the fact that many diabetics suffer from peripheral neuropathy and thus cannot feel pain. Because pain is often a primary incentive for patient compliance, neuropathy patients frequently do not comply with voluntary off-weighting techniques, resulting in further deterioration of the wound and possibly leading to infection.

One common cycle for this medical complication is chronic foot ulceration, infection, hospitalization, amputation and rehabilitation. This costly cascade of events need not take place because two-thirds of diabetic amputees do have an adequate blood supply to heal ulcerations. One significant factor for effective treatment can often be to offload the patient's weight from the ulcerated site to give the ulcers an opportunity to heal.

While some devices have been specifically designed to address the need to treat patients suffering plantar ulcers, it should also be noted that a number of related adjustable leg casts have also been developed. Such casts, however, are often designed primarily for fracture care rather than for treating plantar ulcers. Existing devices for treating plantar ulcerations are often time-consuming to apply and/or relatively expensive.

SUMMARY

Embodiments of the present invention include an apparatus for encouraging compliance with a prescribed orthotic treatment, including an orthotic device applied to a limb of a user, a strap coupled to the orthotic device, where the strap has two ends and wraps around the orthotic device at an attachment area. According to such embodiments, a length along the strap from one end to the other is smaller than a maximum circumference of the limb distal to the attachment area. Embodiments of such an apparatus include a locking mechanism configured to lock the two ends of the strap together.

According to some embodiments of the present invention, the orthotic device is a rigid boot with a footbed and two side struts, each of the two side struts having a strap aperture, and the strap is coupled to the rigid boot through the strap apertures. The orthotic device may further include a hardenable cast applied beneath the rigid boot. One end of the strap may include a female element of a side-release interlocking buckle, and the other end of the strap may include a male element of the side-release interlocking buckle. According to some embodiments of the present invention, the locking mechanism is a combination lock mechanism configured to hold the female element and the male element in an interlocking position unless a particular combination is selected; according to other embodiments of the present invention, the locking mechanism is a key lock mechanism configured to hold the female element and the male element in an interlocking position unless a particular key is used to unlock the key lock mechanism.

According to some embodiments of the apparatus, the strap is adjustable in length. For example, the strap may be a woven nylon strap with one or more melted stripes at lengthwise intervals, such that cutting the strap at or near one of the melted stripes minimizes fraying of the strap. According to some instances of the embodiments, at least one of the plurality of melted stripes is not generally perpendicular to the strap.

Embodiments of the present invention include a method for treating plantar ulcerations, including applying a hardenable cast to a foot of a patient, conforming the cast to the foot prior to hardening of the cast, providing a rigid outer boot having a footbed and two side struts, each of the two side struts having a strap aperture, and strapping the rigid outer boot around the hard cast through the strap apertures. Such embodiments of methods may further include forming a wound window in the hardenable cast through which a wound may be observed or dressed. According to some instances of the embodiments, forming the wound window includes cutting a flap in the hardenable cast near or over the wound; in other instances of the embodiments, forming the wound window includes cutting a hole in the hardenable cast near or over the wound. In some cases, when a hole is cut into the cast to create the wound window, the embodiments of the methods may further include plugging the hole with a bolstering dressing which contacts the inner surface and the outer surface of the cast. In some cases, at least a portion of the bolstering dressing may be reusable.

Embodiments of the present invention include a system for off-weighting a user's foot, including a hardenable cast, a rigid outer boot having a footbed, two side struts each with a strap aperture, and a strap extending through the strap apertures and operable to tighten around the hardenable cast. Such embodiments may further include a rocker bottom, and the hardenable cast may include a tubular mesh, woven of an elastic yarn and a coarse impregnable yarn, and impregnated with a hardening agent. According to some embodiments, the strap is a woven nylon strap and includes one or more melted stripes at lengthwise intervals, such that cutting the strap at or near one of the plurality of melted stripes minimizes fraying of the strap. According to some embodiments, the water- or air-activated hardenable cast includes a wound window through which a wound may be observed and/or dressed. For example, the wound window may be a flap formed in the hardenable cast, the flap configured to open and close, with embodiments of the system further comprising a bolstering dressing configured to fill a gap between the flap and the wound.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 5 illustrates an alternative strap locking mechanism in an open position according to embodiments of the present invention.

FIG. 6 illustrates the alternative strap locking mechanism of FIG. 5 in a closed position, according to embodiments of the present invention.

Figure 1:
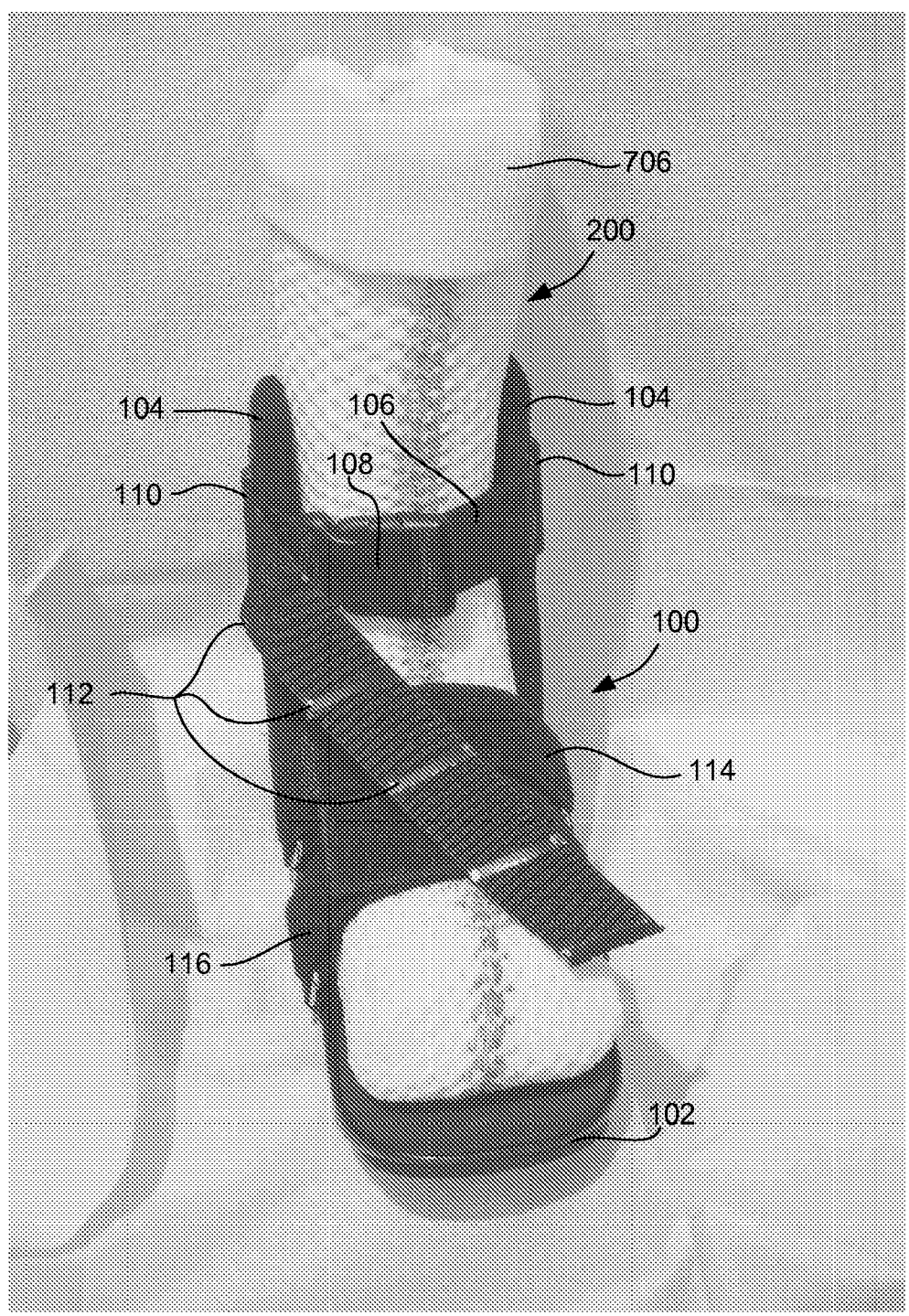
FIG. 1 illustrates a front perspective view of a hard inner cast and rigid outer boot according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
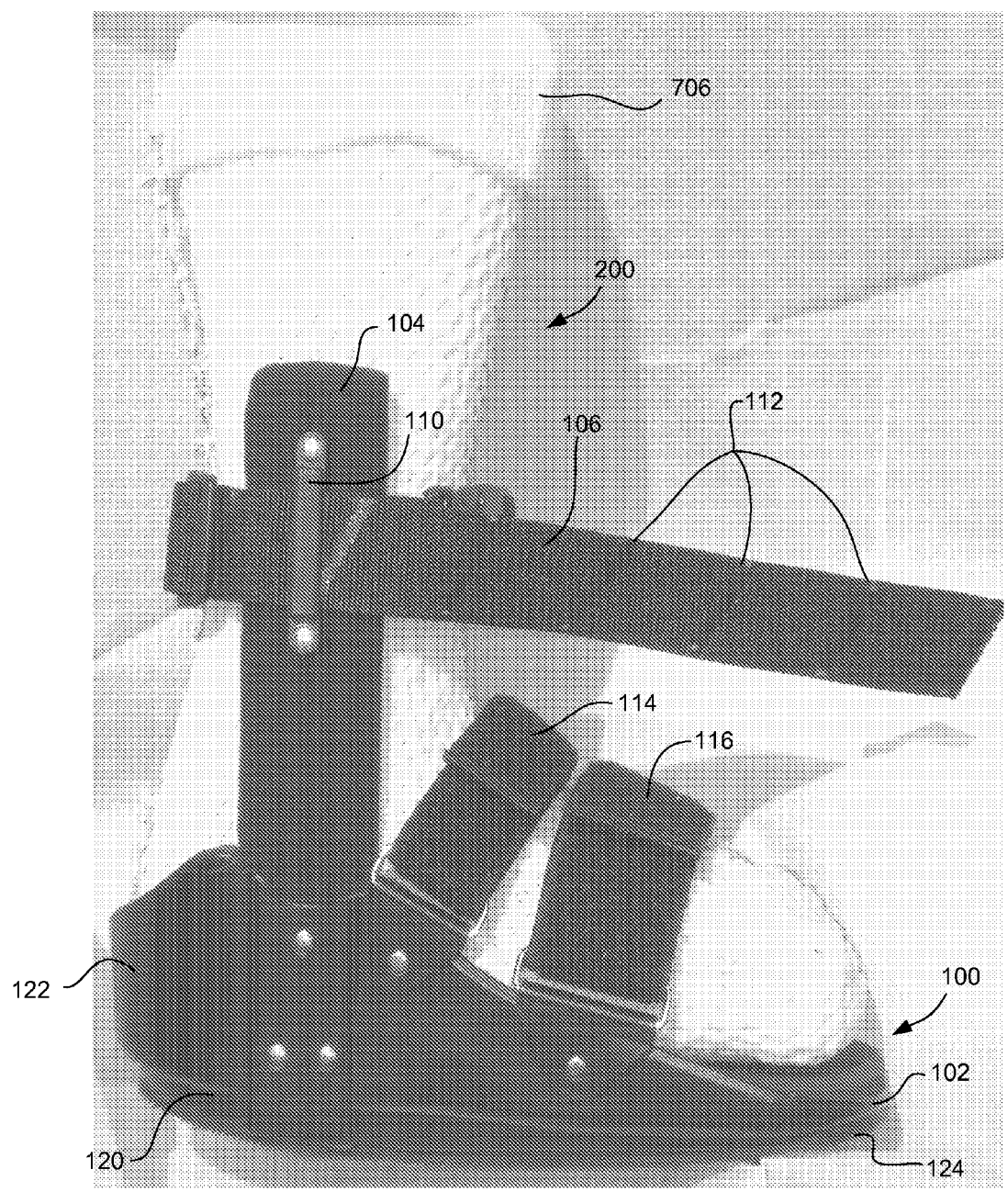
FIG. 2 illustrates a side elevation view of the hard inner cast and rigid outer boot of FIG. 1, according to embodiments of the present invention.

FIG. 1 depicts a front perspective view, and FIG. 2 depicts a side elevation view, of an off-weighting system according to embodiments of the present invention. A hardenable inner cast 200, along with an inner layer of conformable protective padding 706, may be applied to a patient's leg and/or foot, and the hardenable inner cast 200 may placed within a rigid outer boot 100, according to embodiments of the present invention. Conformable protective padding 706 may provide special padding on a patient's heel, arches (dorsal and plantar), ankle bones, tibia, toes, and may provide skin protection during curing of the hardenable inner cast 200, according to embodiments of the present invention. Outer boot 100 includes a rigid footbed 102 to which two side struts 104 are coupled, according to embodiments of the present invention. Foot straps 114, 116 and strap 106 secure the outer boot 100 to the hard cast 200, and strap holders 110 create an aperture in each side strut 104 through which strap 106 passes for coupling the struts 104 to the inner cast 200. Strap 106 includes a buckle 108 for coupling the strap 106 with itself around the inner cast 200. According to some embodiments of the present invention, strap 106 is adjustable in length to accommodate coupling the side struts 104 to casts 200 of different diameter. As used herein, the term "coupled" is used in its broadest sense to refer to elements which are connected, attached, and/or engaged, either directly or integrally or indirectly via other elements, and either permanently, temporarily, or removably.

According to the embodiment depicted in FIGS. 1 and 2, strap 106 is folded back on itself and the length of strap 106 may be adjusted either before or after buckling of buckle 108. Excess length of the strap 106 may protrude from the boot 100; according to embodiments of the present invention, the strap is a woven nylon strap and the end of strap 106 includes one or more melted stripes 112 separated by lengthwise intervals as depicted in FIGS. 1 and 2. Melted stripes 112 present ideal locations for the excess strap 106 material to be cut; cutting the strap 106 at or near the melted stripes 112 minimizes fraying of the strap 106 at the cut location and minimizes the sharp edges that may often be created by singeing the end of strap 106 after cutting, and also creates a roughly triangular end shape for easier feeding through the strap holders 110 and/or other slots designed to keep the end of strap 106 from becoming an annoyance. Strap 106 may be cut to length either before or after buckling of buckle 108 or tightening of strap 106 around cast 200.

Outer boot 100 includes, according to embodiments of the present invention, a substantially vertical sidewall portion 122 and a curved rocker sole 120 with a tread 124 of rubber or the like. Curved rocker sole may increase stability and facilitate off-loading of the patient's foot, according to embodiments of the present invention. Side struts 104 may be riveted to footbed 102 as depicted in FIG. 2; alternatively, side struts may be formed integrally with footbed 102. According to yet other embodiments of the present invention, side struts 104 are removably yet rigidly coupled with footbed 102. When strap 106 is securely and/or snugly fastened around struts 104 and cast 200, part of a patient's weight during standing and/or ambulation is transferred through cast 200 into struts 104 and eventually into footbed 102 for enhanced off-loading of the patient's foot. Acting together, the hard inner cast 200 coupled with the hard outer boot shell 100 serve to more effectively protect and off-load a patient's wound site with a relatively easy-to-apply orthotic kit, while permitting patient ambulation.

Figure 3:
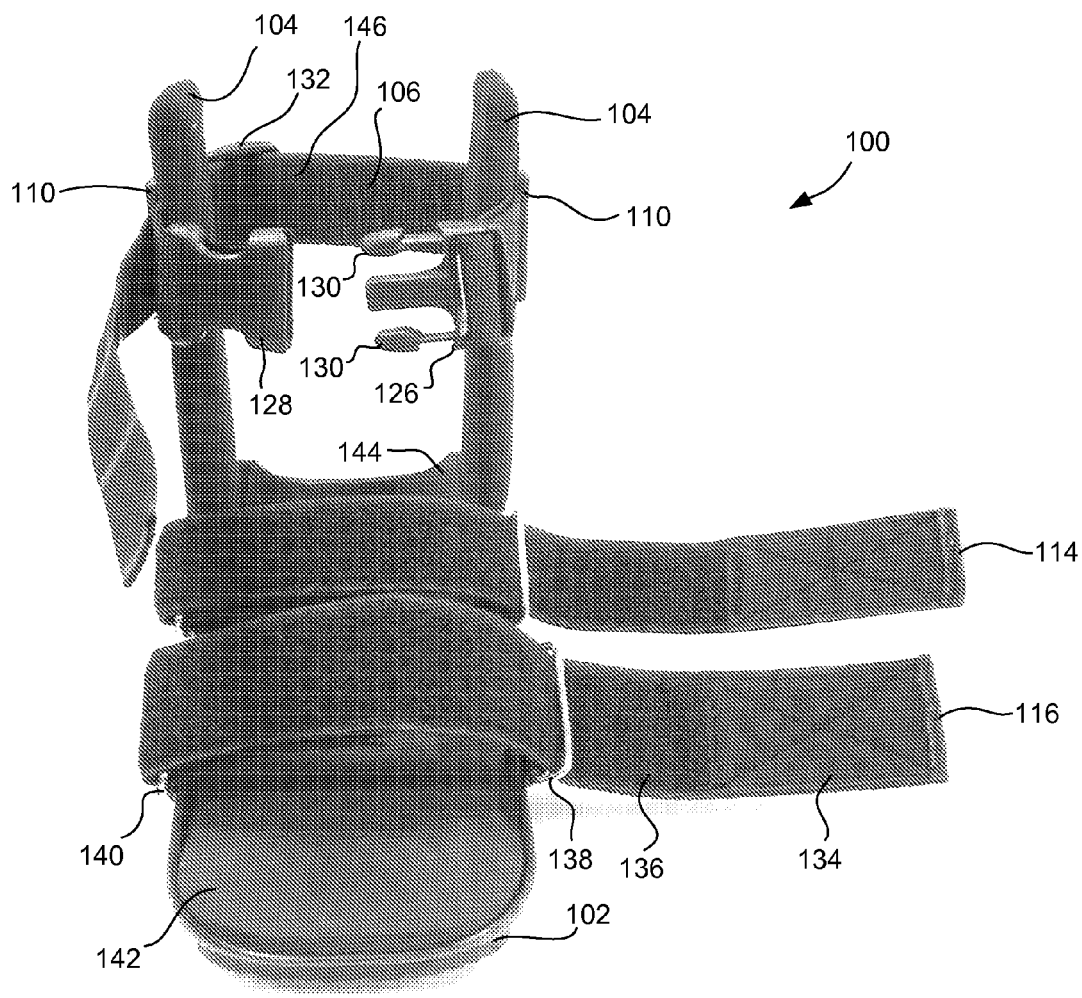
FIG. 3 illustrates a front perspective view of the rigid outer boot of FIGS. 1 and 2 in an open position, according to embodiments of the present invention.

FIG. 3 illustrates a rigid outer boot portion 100 in an open position, according to embodiments of the present invention. As seen in FIG. 3, footbed portion 102 may include foam or rubber padding 142 or the like along the top inner surface of footbed 102 and padding 144 along the inner surface of the raised sidewall 122. Straps 114, 116 may include hook-and-loop fastener portions for adjustable coupling over the forefoot portion of cast 200. For example, strap 116 may be a nylon strap which includes a portion 134 covered with hook-type material and a portion 136 covered with loop-type material, such that strap 116 may be tightened over a user's foot and the hook portion 134 securely fastened to the loop portion 136 to hold the strap 116 in place. Such hook-and-loop type fastening characteristics may also be used to couple strap 116 around foot strap apertures 138, 140. Strap 114 may operate in a similar fashion, according to embodiments of the present invention. Footbed portion 102 may also include a step sensor and/or a pressure sensor to measure patient activity, device presence, and/or pressure with the off-loading device according to embodiments of the present invention.

Buckle 108 may include a male buckle portion 126 at one end of strap 106 with one or more prongs 130 and a female buckle portion 128 at another end of strap 106 configured to receive the one or more prongs 130, according to embodiments of the present invention. Such a buckle 108 is commonly referred to as a side-release interlocking buckle. Strap 106 may also include a slider 132 to facilitate adjustment of the strap 106 length around struts 104. According to some embodiments of the present invention, struts 104 may be covered with a loop-type material and an inside portion 146 of strap 106 may be covered with a hook-type material to engage with one or more of the struts 104 to discourage sliding and/or movement of strap 106 with respect to struts 104 after application.

Figure 4:
FIG. 4 illustrates a front perspective view of the rigid outer boot of FIGS. 1-3 in a closed position, according to embodiments of the present invention.

According to some embodiments of the present invention, at one end strap 106 is affixed to female portion 128, after which it passes through strap holder 110, through slider 132, through the other strap holder 110, through male portion 126 at the other end, then back through the other strap holder 110, back through slider 132, and back through strap holder 110, where it terminates in the one or more melted stripes 112. FIG. 4 depicts the outer boot shell 100 with the straps 114, 116 closed and the male 126 and female 128 ends of buckle 108 fastened, according to embodiments of the present invention. Based on the disclosure provided herein, one of ordinary skill in the art will appreciate the various ways in which strap 106 may be coupled to itself and/or configured to wrap around struts 104 and cast 200 to snugly engage struts 104 to cast 200.

FIGS. 5 and 6 depict an alternative strap 106 coupling system which encourages patient compliance with a prescribed orthotic treatment, according to embodiments of the present invention. A male portion 126' includes one or more prongs 130' configured for insertion into a female portion 128' which includes side slots 150 configured to receive the one or more prongs 130', according to embodiments of the present invention. Male portion 126' and female portion 128' function similarly to the side-release interlocking buckle 108 described above, with the exception that male portion 126' and female portion 128' comprise a locking mechanism which prevents release of the male portion 126' from female portion 128' unless a specific numeric code has been dialed into the combination wheels 152 of the female portion 128', according to embodiments of the present invention. FIG. 6 depicts the locking mechanism of FIG. 5 with the male portion 126' engaged with the female portion 128', according to embodiments of the present invention.

As depicted in FIGS. 5 and 6, the strap 106 of such embodiments of the present invention may be permanently affixed to the female portion 128' at one end, and then pass through the first strap holder 110, then pass through slider 132, then through the second strap holder 110, then through a slot in male portion 126', back through the second strap holder 110, where it may then be permanently affixed to slider 132. Such a configuration results in a strap 106 whose length may be adjusted between a maximum length where the slider 132 is as close as possible to male end 126', and a shorter length at which the strap 106 fits snugly around struts 104 and the cast 200.

According to some embodiments of the present invention, the length of strap 106 and/or the point or points of permanent affixation may be customized such that the maximum length of strap 106 when male portion 126' is engaged with female portion 128' is shorter than a maximum circumference of a patient's foot and/or leg inserted through the strap 106, such that the patient is unable to remove the patient's foot, or the patient's cast 200 which has been applied to the patient's foot, through the strap 106 without unlocking the buckle and disengaging male portion 126' from female portion 128' (or cutting the strap or breaking the buckles 126', 128', the slider 132, or the strap holders 110). In the embodiment shown, the female combination portion 128' engages with the male portion 126' to form a locking mechanism which permits strap release only when a particular two-digit combination has been selected using the number wheels 152 on female portion 128'; the use of such a locking mechanism with an appropriately-sized strap 106 encourages patient compliance with a prescribed orthotic treatment by making it more difficult for the patient to remove the rigid outer boot structure 100 once it has been applied, according to embodiments of the present invention. A combination lock side-release interlocking buckle as depicted in FIGS. 5 and 6 may be obtained from American Plastics of Tracy, Calif. (part number AP006-combo).

As an alternative to a combination lock side-release interlocking buckle, other interlocking buckles or locking mechanisms may be used, according to embodiments of the present invention. For example, a key-lock mechanism may be used, such that releasing the strap 106 to remove rigid outer boot 100 requires the use of a key to disengage one end of the strap 106 from the other end. Alternatively, a numeric combination lock may be used with one or more digits, or a digital combination lock may be used. Alternatively, a special key or tool may be required for removal of the strap 106, where such special key or tool is provided to and maintained by the medical doctor or technician who applies the boot 100. According to yet other embodiments of the present invention, a disposable strap 106 may be used; for example, a disposable strap 106 may be configured to lock onto itself in a non-reversible way, such that it must be cut and replaced by the medical doctor or technician for each reapplication of the hard cast 200. Based on the disclosure provided herein, one of ordinary skill in the art will appreciate the various locking mechanisms which may be used to lock one end of strap 106 to the other. Such locking mechanisms may be locked by the physician or technician at the time of cast 200 and boot 100 application, to encourage patient compliance with the fully effective and prescribed orthosis (cast 200 and boot 100 combined).

Figure 7:
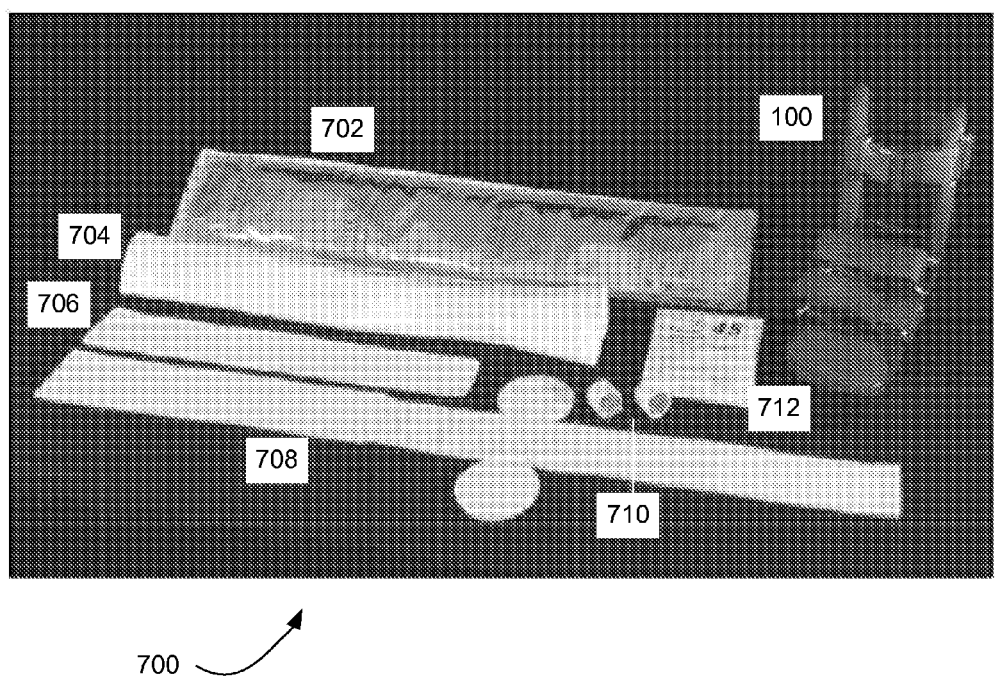
FIG. 7 illustrates a kit for applying a hard inner cast and outer boot according to embodiments of the present invention.

Embodiments of the present invention may be packaged and/or sold as a kit 700, as illustrated in FIG. 7. A kit 700 according to such embodiments may include one or more of a cast sock 702, a protective sleeve 704, a stockinette 706, a tibial crest/malleolar foot pad 708, paper and/or plastic tape 710, a primary dressing 712, and an outer boot 100. According to some embodiments of the present invention, cast sock 702 is a water- and/or air-activated hardenable cast sock which may be applied to a patient's leg while soft and then permitted to harden; cast sock 702 may be composed of a material impregnated with a resin which is water and/or air activated. Cast sock 702 is configured to maintain intimate contact with the user's lower leg, ankle, and foot (dorsal and plantar aspects) which facilitates reduction in shear and plantar pressure redistribution, according to embodiments of the present invention. Cast sock 702 may limit medial and saggital planar motion of the user's ankle and/or foot during treatment, and may be water and/or air activated, breathable (or ventilated by the presence of holes), and easily applied with minimal training, according to embodiments of the present invention.

Cast sock 702 may be, for example, a cast sock part number C4-60 distributed for New Cast Industry Co, Ltd. of Korea by New Cast Industry America, LLC of Reno, Nev. or a tubular mesh, woven of an elastic yarn and a coarse impregnable yarn, and impregnated with a hardening agent as described in U.S. Pat. No. 6,585,671, issued on Jul. 1, 2003, entitled, "Hybrid-Mesh Cast Sleeve and Method," which is hereby incorporated by reference in its entirety. Such a cast sock 702 may be activated by dipping it into water, applying it to the patient, and then permitting it to air dry, according to embodiments of the present invention. Such a cast sock 702 may be pre-packaged to avoid or minimize premature exposure to splashing or to water vapor in the air. Alternatively, cast sock 702 may function similarly while being pre-packaged as a ready-to-apply air-activated hardenable cast. Once cast sock 702 hardens, it becomes hard cast 200 as described above. As used herein, the term "hardenable" is used in its broadest sense to refer to a cast which begins in a pliable and/or semi-pliable state, and which hardens on the patient; for example, a hardenable cast may be a cast which is activated by water, air, ultraviolet radiation, and/or heat, according to embodiments of the present invention.

Figure 8:
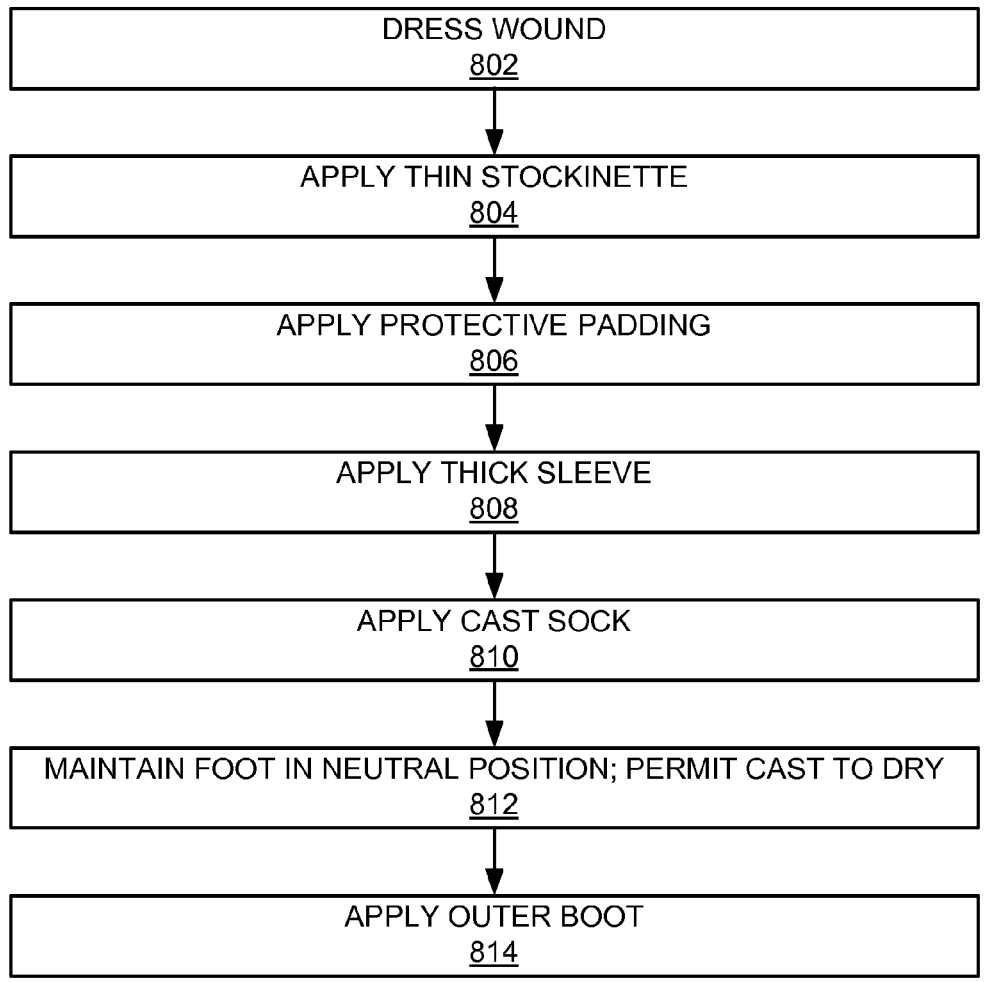
FIG. 8 illustrates a method for applying a hard inner cast and outer boot according to embodiments of the present invention.
Figure 9A:
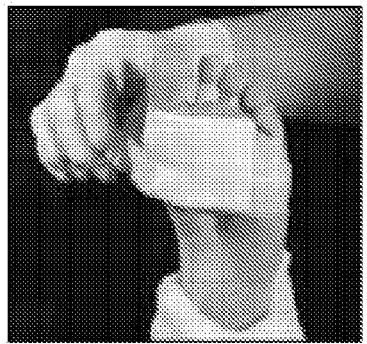
FIGS. 9A-9O illustrates various stages in the application of a hard inner cast and hard outer boot, according to embodiments of the present invention.
Figure 9B:
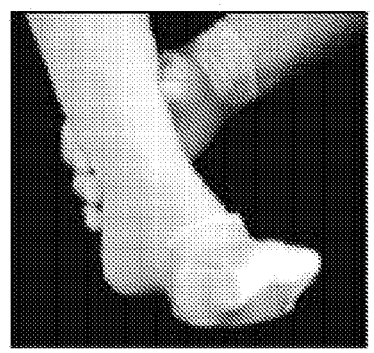
Figure 9C:
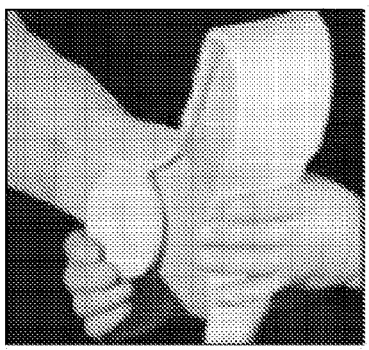
Figure 9D:
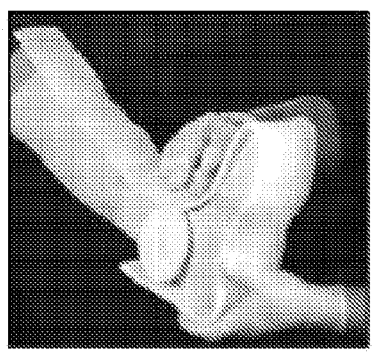
Figure 9E:
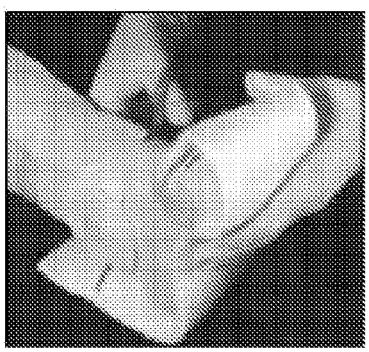
Figure 9F:
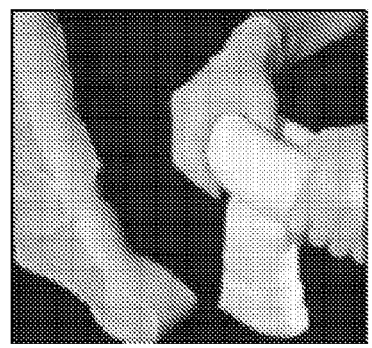
Figure 9G:
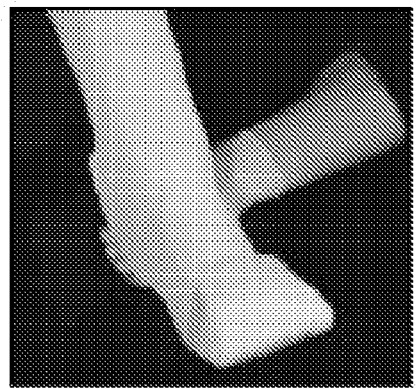
Figure 9H:
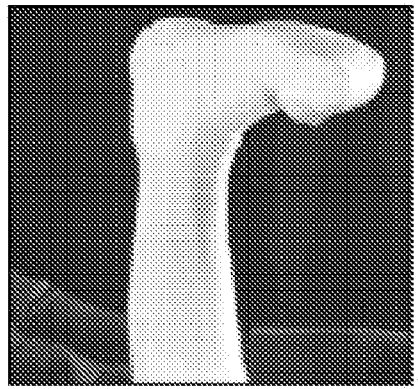
Figure 9I:
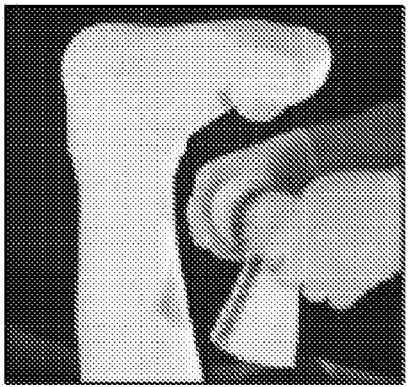
Figure 9J:
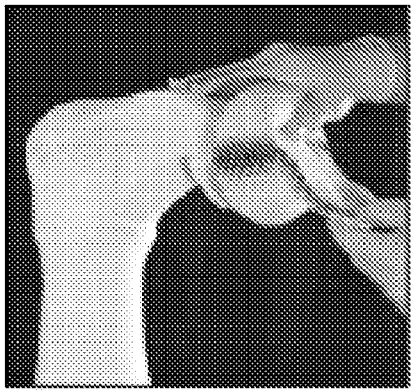
Figure 9K:
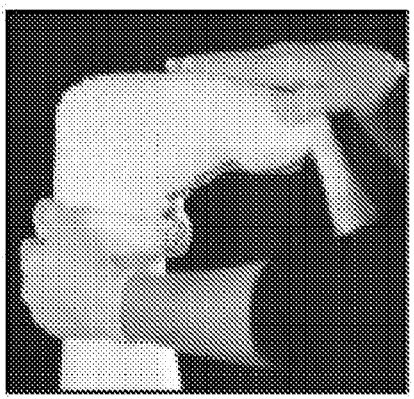
Figure 9L:
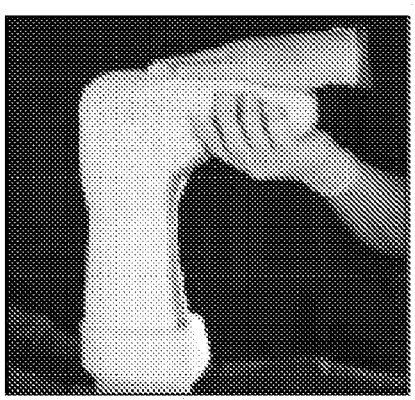
Figure 9M:
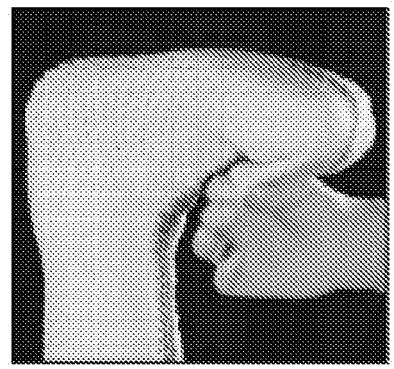
Figure 9N:
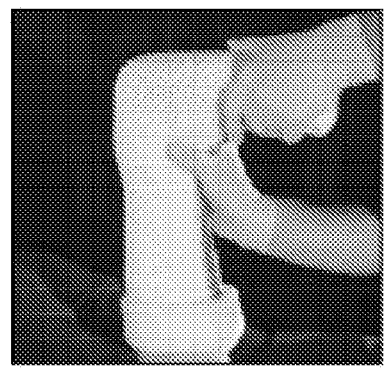
Figure 9O:
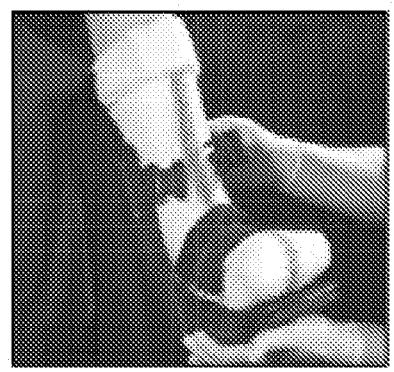

FIGS. 8 and 9A-O illustrate a method for applying an off-weighting system to a patient, according to embodiments of the present invention. FIG. 8 depicts a flow diagram 800 illustrating a method for applying the hard cast 200 portion of the off-weighting system, according to embodiments of the present invention. First, the wound may be dressed (block 802). This may include applying a foam dressing 712 to an ulcer area and securing the dressing 712 with tape, such as, for example, paper tape 710, as illustrated in FIG. 9A. A thin stockinette 706 may then be applied (block 804). This may include pulling the stockinette 706 over the entire foot extending to the patient's knee, while avoiding the disruption of the tape and dressing 712. Excess stockinette 706 may be folded over the dorsum of the foot and secured with plastic tape, and the excess stockinette 706 may be cut, as illustrated in FIG. 9B.

Next, a protective felt padding 708 may be applied (block 806). According to some embodiments of the present invention, this may be accomplished by aligning the circular flaps of the felt padding 708 over the patient's malleoli with the shorter or narrower portion toward the patient's knee, as illustrated in FIG. 9C. Plastic tape may be used to secure the circular pads to the malleoli and strip along the tibia. Remaining protective felt padding 708 may be loosely wrapped to cover the patient's toes and the plantar surface of the patient's foot, as shown in FIG. 9D. The felt padding 708 may be secured in place with plastic tape, and excess padding 708 may be cut to allow for approximately one to three inches of padding 708 beyond the patient's heel, as shown in FIG. 9E.

A relatively thicker sleeve 704, which may be contained in kit 700 in a clear plastic bag, may be applied (block 808). According to embodiments of the present invention, this includes rolling the sleeve 704 into a doughnut shape as illustrated in FIG. 9F, placing the sleeve 704 over the patient's foot, and unrolling the sleeve 704 extending to the patient's knee. The sleeve 704 may be pulled to cover the toes, leaving approximately two to four inches of excess, while ensuring that all previously-applied protective layers have not been disrupted or are otherwise binding the patient's toes. Excess sleeve 704 may be folded over the dorsum of the patient's foot and secured with plastic tape, and the excess sleeve may be cut, as illustrated in FIG. 9G. The excess felt padding 704 may also be cut at the patient's knee and the stockinette 706 folded over the protective sleeve 704.

Prior to applying the cast sock 702, the patient may be placed in a prone position with the patient's leg flexed at the knee, as illustrated in FIG. 9H. The cast sock 702 may then be applied (block 810). According to embodiments of the present invention, this may include rolling the cast sock into a doughnut shape, while leaving approximately two to three inches of unrolled sock 702, as illustrated in FIG. 9I. The cast sock 702 may then be dipped into water, removed from the water, and shaken to remove excess water. Next, the sock 702 may be positioned so that the unrolled end extends beyond the toes by approximately two to three inches, as illustrated in FIG. 9J. Next, the sock 702 may be gently unrolled towards the patient's knee, as illustrated in FIG. 9K. The excess cast sock 702 may be folded back to the widest point of the patient's calf to shorten the cast length, and the proximal edge of the stockinette 706 may be rolled distally to cover loose edges as desired. The patient's foot should then immediately be placed in a ninety-degree neutral position, as illustrated in FIG. 9L. If necessary, the technician applying the cast sock 702 may slide fingers between the patient's dorsal arch and the sock 702 to smooth out wrinkles in any layers. The excess sock 702 may be folded over the dorsum of the patient's foot, as illustrated in FIG. 9M, and wet gloves may be used to contour the cast sock 702 to the patient's leg, ankle area, arch, and Achilles tendon, as illustrated in FIG. 9N, before the cast sock 702 has hardened into the hard cast 200.

Once sock 702 has been applied, the patient's foot should be maintained in a neutral position and the cast permitted to dry (block 812). According to some embodiments of the present invention, the application of the cast sock (block 810) may be highly sensitive to time and temperature. For example, the optimum water temperature (for the water into which the sock 702 is dipped) for ease of use is seventy-two degrees Fahrenheit. The recommended water temperature range is sixty-eight to seventy-seven degrees Fahrenheit, or twenty to twenty-five degrees Celsius. Cooler water may slow the speed of cast sock 702 hardening and reduce elasticity, while warmer water may increase the speed of hardening and may make the cast sock 702 too elastic and/or difficult to use. If the recommended water temperature is used, the cast may be allowed to dry for approximately seven minutes or until the area of the cast 702 is cool and hardened. If water of a cooler temperature has been used, the cast 702 should be allowed to dry approximately ten minutes or until the toe area of the cast is cool and hardened, according to embodiments of the present invention. The patient may return to a seated position during drying of the cast sock 702.

Once the cast sock 702 has hardened into hard cast 200, the outer boot 100 may be applied (block 814). As described above, this may include placing the hardened cast sock 702 between upright struts 104 of the walker boot 100, ensuring that the struts 104 are substantially aligned with (or parallel to) the patient's tibia and fibula as illustrated in FIG. 9O, and then securing the toe strap 116, ankle strap 114, and then strap 106 to keep the rigid boot 100 positioned properly relative to the patient's leg during ambulation, and then allowing the patient to weight bear, according to embodiments of the present invention. Although various procedures have been described with respect to flow diagram 800, one of ordinary skill in the art, based on the disclosure provided herein, will recognize that some steps may be performed in different orders, and that less than all of the described steps or additional steps may be performed, according to embodiments of the present invention.

According to some embodiments of the present invention, for a calf circumference of thirteen to seventeen inches a cast sock 702 that measures approximately three inches in diameter by approximately sixty centimeters in length may be used, and for a calf circumference of seventeen to twenty-four inches, a cast sock 702 that measures approximately four inches in diameter by approximately sixty centimeters in length may be used. According to embodiments of the present invention, the rigid outer boot 100, including the footbed 102 and/or side struts 104, may be constructed of a plastic; side struts 104 may also be wholly or partially made of aluminum. Straps 106, 114, 116 may be constructed wholly or partially of nylon and/or heavyweight polypropylene; straps 106 and 114 may be approximately one and one-half inches wide, while strap 116 may be two inches wide, according to embodiments of the present invention.

According to some embodiments of the present invention, the cast 200 forms a hard inner cone or conical area against the patient's calf or lower leg, which, when the patient applies a load to the cast 200, passively operates to compress the patient's leg. The attachment of boot 100 further enhances such a "cone-within-a-cone" type of compression, which operates to substantially deter or minimize fluid accumulation in the patient's leg.

Due to the relative ease of removal and/or application of cast 200, the patient's cast 200 may be changed or replaced periodically. In fact, the cast 200 may necessitate periodic replacement as the patient's leg size changes due to swelling or other similar factors. However, an ability to inspect and/or dress a patient's wound may be desirable even without removing the cast 200, according to embodiments of the present invention.

Figure 10:
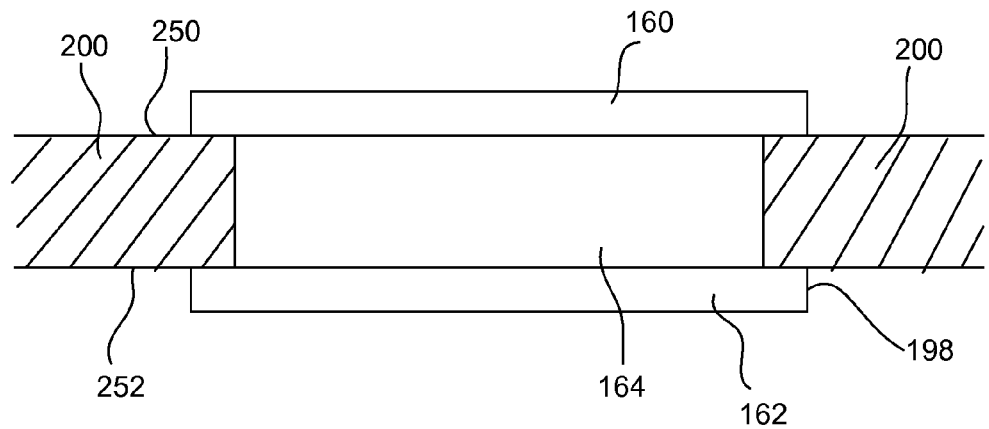
FIG. 10 illustrates a partial side cross-sectional view of a wound window formed in a hard cast and a bolstering dressing, according to embodiments of the present invention.
Figure 11:
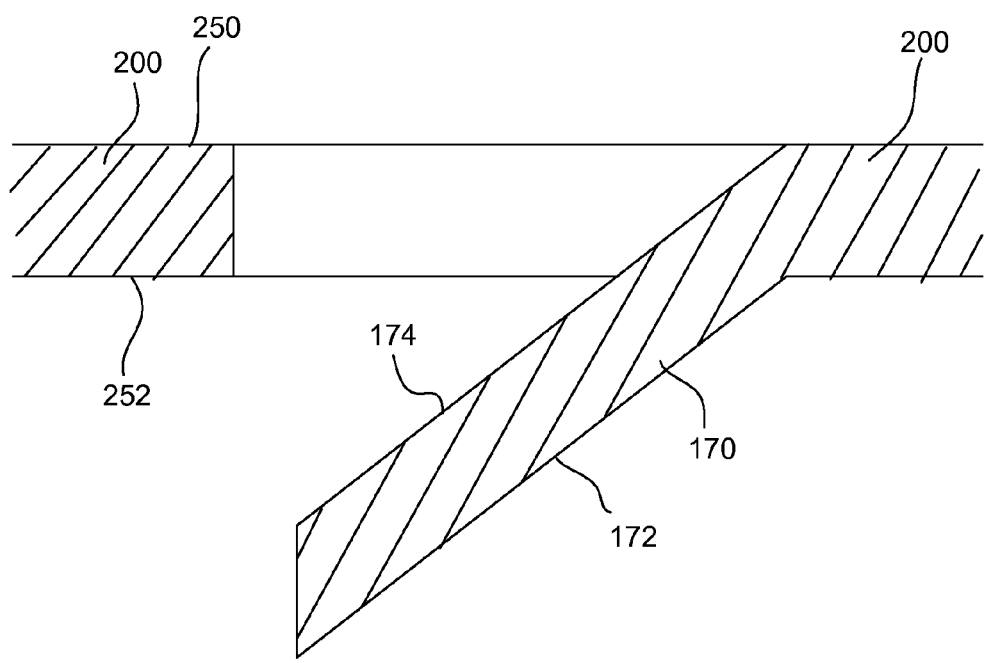
FIG. 11 illustrates a partial side cross-sectional view of a wound window flap formed in a hard cast, according to embodiments of the present invention.

FIGS. 10 and 11 illustrate wound access windows, according to embodiments of the present invention. According to some embodiments of the present invention, a hole may be cut in the bottom of cast 200 under the patient's wound, without removing the cast. This may be accomplished with a cast saw, for example. According to some embodiments of the present invention, the hole may be cut prior to hardening of the cast 200 by scissors, knife, and/or any other type of cutting device. Such a hole may permit the inspection and/or dressing and/or re-dressing of the wound, without removal of the entire cast 200. Once the inspection and/or dressing of the wound has occurred, the hole in the cast 200 may be plugged or otherwise filled with a bolstering dressing 198 or the like. Bolstering dressing 198 primarily includes a center portion 164 configured to fill or plug the hole created in the cast 200. Bolstering dressing 198 may further include a proximal flange 160 configured to abut the proximal surface 250 of cast 200 near the patient's wound and/or a distal flange 162 configured to abut the distal surface 252 of cast 200. Proximal flange 160 and/or distal flange 162 are configured to hold bolstering dressing 198 in place, according to embodiments of the present invention.

According to some embodiments of the present invention, proximal flange 160 is flexible or semi-flexible, such that bolstering dressing 198 may be pushed into the cast window from the distal end until the proximal flange 160 expands outwardly to contact the proximal surface 250. According to some embodiments of the present invention, the proximal flange 160 and/or distal flange 162 are removably coupled with the center portion 164 (e.g. with a threadable and/or hook-and-loop and/or pressure-fit connection); according to other embodiments the proximal flange 160, distal flange 162, and/or center portion 164 are formed as one integral piece. According to yet other embodiments of the present invention, distal flange 162, center portion 164, and/or proximal flange 160 are reusable and/or replaceable. For example, center portion 164 and/or distal flange 162 may be reusable while proximal flange 160, as being situated close to or against the wound site, may be replaced each time the wound is accessed through the cast window or hole, according to embodiments of the present invention. Although shown as protruding slightly from proximal surface 250 and distal surface 252, bolstering dressing 198 may alternatively be configured to be substantially flush with proximal surface 250 and/or distal surface 252, according to embodiments of the present invention. According to some embodiments of the present invention, proximal flange 160 and/or entire bolstering dressing 198 may be designed to be replaced with a different type or thickness of dressing and/or padding depending on the patient's stage of healing.

FIG. 11 illustrates an alternative wound window, according to embodiments of the present invention. Instead of a hole drilled into cast 200, a flap 170 may alternatively be formed in cast 200. This may be accomplished with a cast saw, for example. Flap 170 may be cut in the shape of a simple three-sided square, for example, with the fourth side representing the "hinge" area where the flap 170 is bent outwardly (e.g. distally) to permit access to the wound site, as illustrated in FIG. 11. The flap 170 may alternatively be formed in other shapes, as necessitated or made desirable by the shape of the wound and/or the size of the access window needed. According to some embodiments of the present invention, a double-flap may be used to open distally like a pair of window shutters on a house. The proximal surface 174 of flap 170 may be configured to abut the wound site and/or the wound dressing; the flap 170 of FIG. 11 may be secured shut after the wound inspection or re-dressing has been accomplished by taping the distal surface 172 of the flap 170 to the distal surface 252 of cast 200, according to embodiments of the present invention. According to some embodiments of the present invention, a bolstering dressing similar to bolstering dressing 198 of FIG. 10 may be inserted between proximal surface 174 of flap 170 and the patient's wound, in order to maintain the healing process while adequately cushioning the wound during ambulation, despite the presence of the wound window and/or flap 170. Based on the disclosure provided herein, one of ordinary skill in the art will recognize the various ways in which flap 170 may be created and/or secured back in place in cast 200, including the use of clips, latches, and the like.

Figure 12:
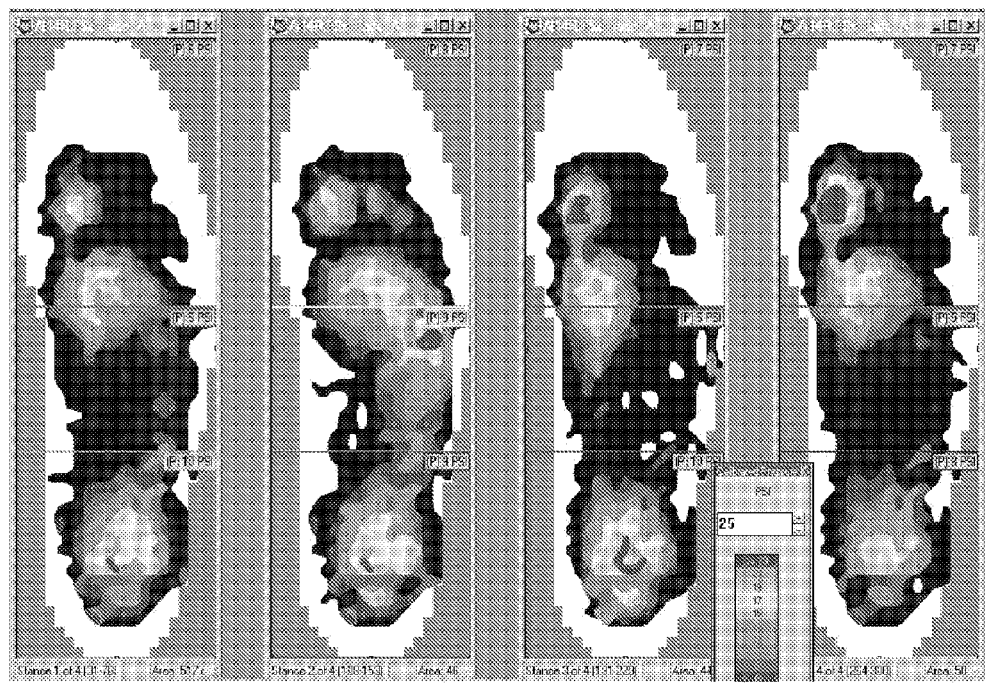
FIG. 12 illustrates a pressure plot of an average plantar pressure over three areas of a foot for each of four steps for a user wearing a hard cast and rigid outer boot, according to embodiments of the present invention.

FIG. 12 illustrates a pressure plot of the average plantar pressure over three areas of a foot for each of four steps for a user wearing the hard cast 200 and rigid outer boot 100 according to embodiments of the present invention. FIG. 12 demonstrates that the use of hard cast 200 and rigid outer boot 100 does effectively and substantially off-load the plantar area of a patient's foot.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for treating plantar ulcerations, the method comprising:
    applying a hardenable cast to a foot of a patient;
    conforming the cast to the foot prior to hardening of the cast;
    providing a rigid outer boot having a footbed and two side struts, each of the two side struts having a strap aperture; and
    strapping the rigid outer boot around the hard cast through the strap apertures.

2. The method of claim 1, further comprising forming a wound window in the hardenable cast through which a wound may be observed or dressed.

3. The method of claim 2, wherein forming the wound window comprises cutting a flap in the hardenable cast near or over the wound.

4. The method of claim 2, wherein forming the wound window comprises cutting a hole in the hardenable cast near or over the wound.

5. The method of claim 4, wherein the hardenable cast includes a proximal inner surface and a distal outer surface, the method further comprising:
    plugging the hole with a bolstering dressing, wherein the bolstering dressing contacts the inner surface and the outer surface.

6. The method of claim 5, wherein at least a portion of the bolstering dressing is reusable.

7. The method of claim 1, wherein conforming the cast to the foot comprises forming the cast to a lower leg of the patient in a substantially conical shape, such that applying weight to the cast compresses the lower leg to deter fluid accumulation.

8. A system for off-weighting a user's foot, the system comprising:
    a hardenable cast;
    a rigid outer boot comprising:
        a footbed;
        a first side strut having a first strap aperture; and
        a second side strut having a second strap aperture; and
    a strap extending through the first strap aperture and the second strap aperture, and operable to tighten around the hardenable cast.

9. The system of claim 8, wherein the footbed comprises a rocker bottom.

10. The system of claim 8, wherein the hardenable cast comprises a tubular mesh, woven of an elastic yarn and a coarse impregnable yarn, and impregnated with a hardening agent.

11. The system of claim 8, wherein the strap is a woven nylon strap, and wherein the woven nylon strap comprises a plurality of melted stripes at lengthwise intervals, such that cutting the strap at or near one of the plurality of melted stripes minimizes fraying of the strap.

12. The system of claim 11, wherein at least one of the plurality of melted stripes is not generally perpendicular to the strap.

13. The system of claim 8, wherein the hardenable cast comprises a wound window through which a wound may be observed and/or dressed.

14. The system of claim 13, wherein the wound window comprises a flap formed in the hardenable cast, the flap configured to open and close, the system further comprising a bolstering dressing configured to fill a gap between the flap and the wound.

15. The system of claim 8, wherein one of the first strut or the strap includes a loop-type material, and wherein the other of the first strut or the strap includes a hook-type material to discourage sliding of the strap with respect to the first strut.

* * * * *